(12) United States Patent
Hilaire et al.

(10) Patent No.: US 10,046,014 B2
(45) Date of Patent: Aug. 14, 2018

(54) USEFUL ACTIVE AGENT FOR PREVENTING AND/OR TREATING DANDRUFF CONDITIONS OF THE SCALP

(75) Inventors: Pascal Hilaire, Vouvray (FR); Yann Mahe, Sainte Genevieve des Bois (FR); Richard Martin, Rochecorbon (FR)

(73) Assignee: L'OREAL, Paris (FR)

( * ) Notice: Subject to any disclaimer, the term of this patent is extended or adjusted under 35 U.S.C. 154(b) by 287 days.

(21) Appl. No.: 14/110,049

(22) PCT Filed: Apr. 5, 2012

(86) PCT No.: PCT/IB2012/051698
§ 371 (c)(1),
(2), (4) Date: Dec. 30, 2013

(87) PCT Pub. No.: WO2012/137170
PCT Pub. Date: Oct. 11, 2012

(65) Prior Publication Data
US 2014/0106016 A1    Apr. 17, 2014

(30) Foreign Application Priority Data

Apr. 5, 2011 (FR) ................................. 11 01029

(51) Int. Cl.
  *A61K 35/74*   (2015.01)
  *A61K 8/99*    (2017.01)
  *A61Q 5/00*    (2006.01)

(52) U.S. Cl.
  CPC ............ *A61K 35/74* (2013.01); *A61K 8/99* (2013.01); *A61Q 5/006* (2013.01); *A61K 2800/70* (2013.01); *A61K 2800/74* (2013.01); *A61K 2800/85* (2013.01)

(58) Field of Classification Search
  CPC .... A61Q 5/006; A61K 35/74; A61K 2800/85; A61K 2800/70
  See application file for complete search history.

(56) References Cited

U.S. PATENT DOCUMENTS

| | | | | |
|---|---|---|---|---|
| 5,795,574 A | * | 8/1998 | Breton | ............ A61K 8/97 424/115 |
| 5,955,321 A | * | 9/1999 | Bijl | ............ A61K 8/673 435/170 |
| 6,242,229 B1 | * | 6/2001 | Pineau | ............ A61K 8/99 435/170 |
| 9,265,719 B2 | * | 2/2016 | Castiel | ............ A61K 8/0216 |
| 2004/0101503 A1 | | 5/2004 | Mahe et al. | |
| 2011/0014246 A1 | | 1/2011 | Elsenreich et al. | |
| 2011/0150952 A1 | | 6/2011 | Simonnet et al. | |

FOREIGN PATENT DOCUMENTS

| | | |
|---|---|---|
| EP | 1 400 237 | 3/2004 |
| EP | 2 149 368 | 2/2010 |
| FR | 2 879 452 | 6/2006 |
| FR | 2 930 443 | 10/2009 |

OTHER PUBLICATIONS

International Search Report dated Jun. 19, 2012 in PCT/IB12/051696 filed Apr. 5, 2012.
French Search Report dated Nov. 22, 2011 in FR 1101029 Filed in Apr. 5, 2011.
Written Opinion dated Jun. 19, 2012 in PCT/IB12/051698 Filed Apr. 5, 2012(with Computer generated translation).
Combined Chinese Office Action and Search Report dated Nov. 2, 2014 in Patent Application No. 201280027476.3 (with summary of analysis and English translation of categories of cited documents).

* cited by examiner

*Primary Examiner* — Vera Afremova
(74) *Attorney, Agent, or Firm* — Oblon, McClelland, Maier & Neustadt, L.L.P.

(57) ABSTRACT

The present invention relates to the cosmetic use of a lysate of a bacterium or bacteria belonging to the *Vitreoscilla* sp. genus (in particular the species: *Vitreoscilla filiformis*) in a complete fermentation medium, as an active agent for preventing and/or treating dandruff conditions of the scalp, including dandruff conditions of the scalp associated with a prevalence of pathogenic microorganisms on the scalp and/or an imbalance of the scalp ecoflora.

8 Claims, 11 Drawing Sheets

USEFUL ACTIVE AGENT FOR PREVENTING AND/OR TREATING DANDRUFF CONDITIONS OF THE SCALP

The invention relates to the cosmetic use of an active agent derived from a microorganism belonging to the *Vitreoscilla* sp. genus (in particular the species: *Vitreoscilla filiformis*) as an active agent for preventing and/or treating dandruff conditions of the scalp, including dandruff conditions associated with a proliferation of pathogenic microorganisms on the scalp and/or an imbalance of the scalp ecoflora.

The skin is a tissue in which the cells are joined together and integrally attached to each other. Skin tissue forms an outer coating comprising sebaceous or sweat glands, and hair follicles. The skin and, in particular, the scalp are epithelia which undergo continual renewal. The renewal, or desquamation, is a coordinated and finely regulated process resulting in the imperceptible and invisible removal of the superficial cells.

However, abnormal or irregular desquamation of the cells of the stratum corneum, for various reasons, can result in the formation of large, thick cell clusters which are visible to the naked eye and called "squamae" or "dandruff" in the case of the scalp, or in other situations in a thinning of the stratum corneum. Desquamation disorders, resulting from abnormal or irregular desquamation, can result in fragility or even in a lack of the barrier properties of the epidermis.

By way of example of factors which promote the appearance of squamae or dandruff, mention may be made of stress, the winter period, an excess of sebum, a moisturization defect, or colonization of the skin or the hair follicles by the yeast *Malassezia* sp. These factors in particular have the common feature of causing and/or promoting skin inflammation. Such an inflammation reinforces the appearance or even increases the presence of squamae or of dandruff. In particular, yeasts of *Malassezia* sp. type, which make up part of the normal commensal flora at the surface of the scalp in dandruff-free individuals, experience a substantial increase in their proportion in the case of dandruff, or in the case of associated seborrheic dermatitis. Imbalance of the scalp ecoflora is a factor that promotes or even reinforces the presence of dandruff.

The presence of squamae or dandruff conditions can be recurring, frequent, chronic conditions which are socially debilitating owing to their obvious unsightly nature. What is more, dandruff conditions of the scalp or abnormal desquamation of the skin can be reflected by an impairment of the barrier function of the epidermis, or generate itching sensations or pruritus, resulting in scratching which amplifies the phenomenon of the appearance of squamae or dandruff, and, in return, irritation of the scalp or the skin.

The dandruff conditions of the scalp may be of oily type or of dry type. Dry dandruff conditions of the scalp are more frequently manifested, and are amplified, during skin moisturization disorders, and in particular during substantial dryness of the scalp epidermis. In addition, since the scalp is rich in sebaceous glands, a dandruff condition can develop more readily in the excessive presence of sebum and be more readily pruriginous. Thus, an excessive secretion of sebum, or hyperseborrhea, promotes the appearance of an oily dandruff condition of the scalp, or oily dandruff, generally associated with displeasure, sensations of discomfort, esthetic disorders, or even a cutaneous pathological condition.

Dandruff conditions generally respond to various local or systemic treatments. However, the efficacy of these treatments is only suspensory and demands rigorous adherence on the part of the user (sufficient frequency of use and sufficient application time). However, daily and long-term use of these treatments can lead to a phenomenon of habituation, reducing their efficacy, the habituation generally being associated with a rebound phenomenon occurring when the treatment is stopped. This phenomenon manifests itself through hyperseborrhea, which worsens the dandruff condition and impairs the barrier function of the scalp. Moreover, the aggressiveness of certain antidandruff active agents with respect to the epidermal cells or the scalp ecoflora may also affect the scalp's barrier functions and lead to worsening of the dandruff condition. Finally, the efficacy of antidandruff treatments is often slow to develop and requires rigorous application over the long term. This lag time often leads to failure to follow the treatment. Consequently, many failures arise in the use of these treatments.

Many epidermal factors, the expression, biological activity or maturation of which are modified, decreased or increased, are known to be involved, directly or indirectly, in the process of renewal or desquamation of the scalp.

These factors can be used as biomarkers for the scalp, as screening targets, or even as cosmetic active agents.

However, many unknown factors still remain regarding the intimate mechanism and the factors involved in desquamation of the skin, and in particular in the onset of dandruff.

There is also a need for novel active agents or novel treatments for preventing and/or treating a skin desquamation disorder, and more particularly a dandruff condition of the scalp.

There is also still a need for novel cosmetic treatments for preventing, reducing and/or treating dandruff conditions of the scalp, which are efficient and free of side effects liable to adversely affect good adherence to the treatment.

There is also a need for a cosmetic treatment for dandruff conditions of the scalp that does not adversely affect the scalp ecoflora, or even that reinforces the presence of a healthy ecoflora.

There is a need for cosmetic treatments for dandruff conditions that are capable of maintaining, or even reinforcing, the barrier properties of the scalp.

There is a need for cosmetic treatments for dandruff conditions that are free of the abovementioned side effects, and in particular that do not induce hyperseborrhea, seborrheic dermatitis or pruriginous conditions.

There is also a need for a cosmetic treatment for dandruff conditions that does not induce inflammation.

It is an object of the present invention to satisfy these needs.

Thus, the present invention aims in particular to provide a novel active agent which meets the abovementioned requirements and which in particular shows an effectiveness with regard to the disorders of the barrier function of the scalp in the face of a pathogenic microflora. As is described in detail hereinafter, the novel active agent of the invention is advantageously used in the implementation of cosmetic treatment processes for dandruff conditions of the scalp.

Figure 1:
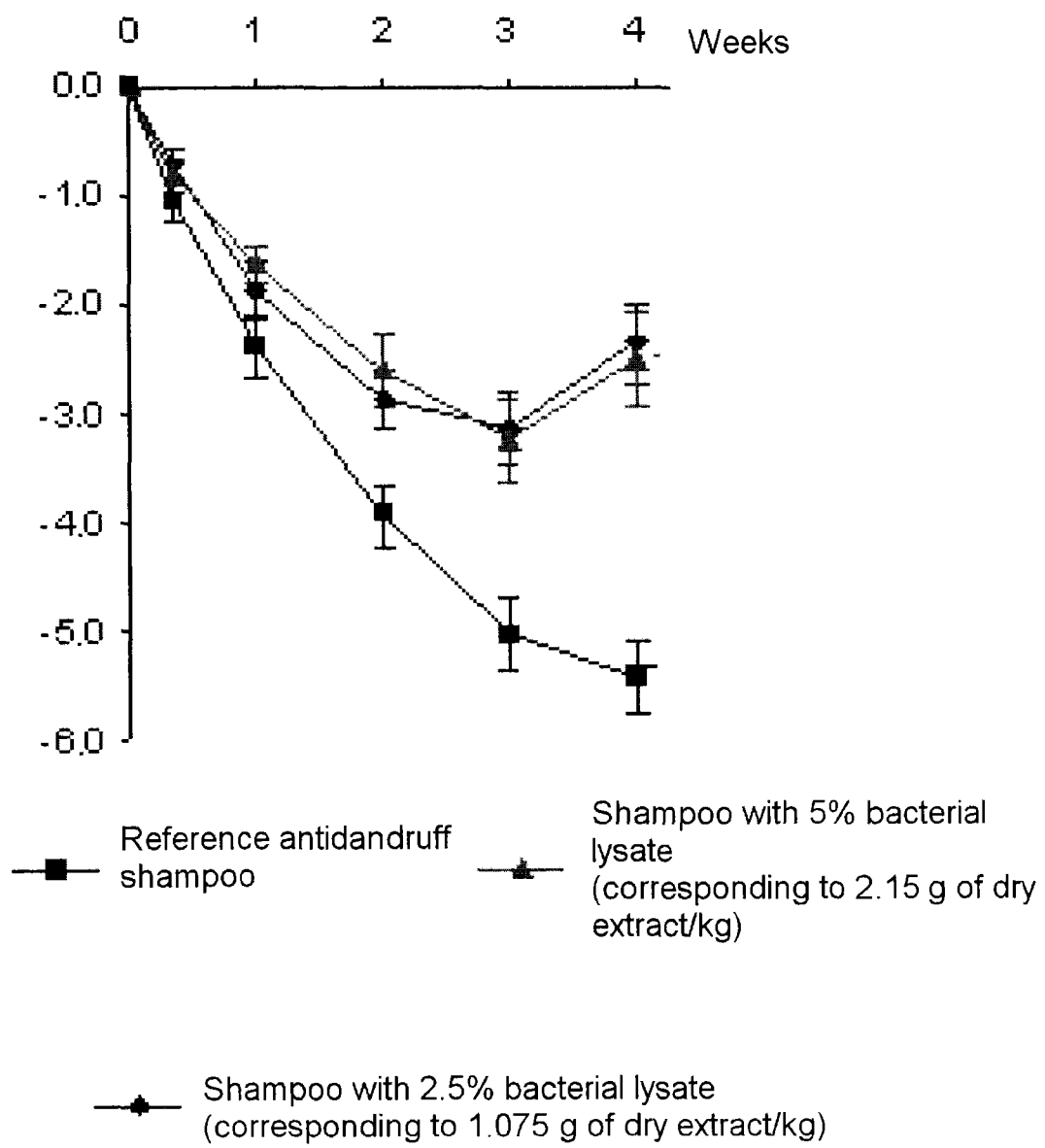
FIG. 1 shows the results of the comparison of the effects on the dandruff of (i) a. shampoo comprising an isolated bacterial lysate, free of complete fermentation medium, used at 2.5% by weight (corresponding to 0.1075% of dry extract), (ii) a shampoo comprising an isolated bacterial lysate, free of complete fermentation medium, used at 5% by weight (corresponding to 0.215% of dry extract), and (iii) the reference antidandruff shampoo formula.

More specifically, the present invention relates to the cosmetic use of a lysate of a bacterium or bacteria belonging to the *Vitreoscilla* sp. genus (in particular the species: *Vitreoscilla filiformis*), in a complete fermentation medium, as an active agent for preventing and/or treating dandruff conditions of the scalp, in particular associated with an imbalance of the scalp ecoflora.

The prevention and/or treatment of dandruff conditions encompass the prevention and/or treatment of dandruff and/or the prevention and/or treatment of itching of the scalp linked to the presence of dandruff.

For the purposes of the present invention, the expression "lysate in a complete fermentation medium" means that the lysate is used and is present, in the cosmetic or dermatological composition containing it, formulated in its complete culture medium of origin as defined hereinafter, which complete culture medium is the medium in which the bacteria were cultured until after the microbial growth phase having resulted in the use of the nutritive substrates initially present in the culture medium.

For the purposes of the present invention, the expression "complete fermentation medium" is intended to denote a medium resulting from the culturing process having been used for the growth and the cell lysis of the microorganism, said medium having undergone, moreover, no additional manipulation aimed at separating and/or removing all or part of its nonaqueous constituents.

For the purposes of the present invention, the term "preventing" means totally eliminating or partially reducing the risk of manifestation of a given phenomenon, i.e. in the present invention the manifestation of dandruff conditions of the scalp. "Partial reduction" implies that the risk remains but to a lesser degree than before the implementation of the invention.

A composition containing the active agent according to the invention can be administered topically.

The application of an extract of non-photosynthetic, non-fruiting filamentous bacteria, like bacteria of the *Vitreoscilla* sp. genus (in particular the species *Vitreoscilla filiformis*), as an active agent for modulating and preferably inhibiting the adhesion and/or the proliferation of pathogenic microorganisms on the skin and the scalp has already been proposed in document FR 2 879 452.

However, the extract under consideration in that document consists of either the supernatant of the fermentation medium of said bacterium, or the biomass obtained after culturing said bacteria, or the envelopes or envelope fractions or else extracts obtained following a supplementary treatment of the biomass. Consequently, all of the above-mentioned extracts are obtained only after a supplementary operation such as, for example, filtration or centrifugation, applied to the fermentation medium for the purpose of separating the extract under consideration from the other constituents of this fermentation medium.

The active agent under consideration according to the invention is therefore completely different than the extract under consideration and described in document FR 2 879 452.

Cosmetic and/or dermatological compositions comprising a total extract of *Vitreoscilla filiformis* have been described in European patent application No. EP 1 400 237. Application EP 1 400 237 describes various extracts of *Vitreoscilla filiformis*, respectively (i) bacterial cells separated from the biomass, for example by centrifugation, (ii) the biomass, which is a noncellular suspension that may contain cell debris, and (iii) the supernatant fraction of this biomass.

As opposed to the extract described in FR 2 879 452 or else to those described in EP 1 400 237, the active agent under consideration according to the invention consists of all the components present in the fermentation medium. The surprising effect of the use according to the invention therefore results from the use, as active agent, for the first time by the inventors of a microorganism lysate in its complete fermentation medium.

Indeed, and as emerges from the examples hereinafter, the inventors have noted that the active agent in accordance with the invention shows a regulatory activity on the scalp microflora which is greater than that noted for a biomass-type extract of the same bacterium. In particular, the inventors have observed that, after a treatment of the invention, the balance of the microflora and the barrier properties of the scalp are reinforced.

Without wishing to be bound by what follows, this gain in effectiveness could be the result of a synergistic effect between constituents of the bacterium, which are normally separated from one another, for example its water-soluble metabolites, generated during its proliferation in its fermentation medium and conventionally present in the aqueous supernatant, and its components such as non-water-soluble cell envelopes or cell envelope fractions constituting all or part of the biomass of its culture medium, or even its isolated lysate.

It has thus been shown in the examples that a cosmetic composition comprising an active agent according to the invention (a lysate of bacteria belonging to the *Vitreoscilla* sp. genus in a complete fermentation medium) has properties of reducing dandruff conditions of the scalp which are equal to or even greater than those of known antidandruff active agents, such as octopirox or zinc pyrithione (ZnPT). In particular, it has been shown in the examples that a cosmetic formulation comprising an active agent of the invention is active against dandruff conditions of the scalp at much lower doses than the doses of conventional antidandruff active agents required for obtaining the same effects on dandruff of the scalp.

It has also been shown that an active agent according to the invention also has properties of reducing itching of the scalp caused by dandruff conditions.

Contrary to all expectations, the active agent according to the invention appears, on the other hand, to be free of any inhibitory activity with regard to the various strains of *Malassezia* sp. studied: *globosa* and *restricta*, as shown in the examples.

According to another embodiment, the present invention relates to a cosmetic process for preventing and/or treating dandruff conditions of the scalp, including dandruff conditions of the scalp associated with a prevalence of pathogenic microorganisms on the scalp and/or an imbalance of the scalp ecoflora in an individual, comprising at least one step of administering to said individual, in particular orally, an effective amount of at least one lysate of a bacterium or bacteria belonging to the *Vitreoscilla* sp. genus (in particular the species: *Vitreoscilla filiformis*) in a complete fermentation medium.

For the purposes of the present invention, the term "effective amount" means a sufficient and necessary amount of the compound under consideration for obtaining the expected effect. Such an amount may be determined by any method known to those skilled in the art, for example by means of preliminary experimental tests.

According to another of its aspects, the present invention relates to a rinse-off or leave-on cosmetic and/or dermatological composition containing, in a physiologically acceptable medium, at least one lysate of a microorganism or microorganisms belonging to the *Vitreoscilla* sp. genus (in particular of the species: *Vitreoscilla filiformis*), in a complete fermentation medium.

Complete Fermentation Medium

As previously stated, the expression "complete fermentation medium" is intended to denote a fermentation or else culture medium which has the same composition, at least in terms of nonaqueous constituents, or even completely, as the fermentation medium in which there was successively carried out the fermentation and the cell lysis of the microorganism devoted to forming the lysate required in parallel according to the invention.

In other words, this medium has undergone, moreover, no secondary manipulation aimed at separating and/or removing all or part of its nonaqueous constituents.

More particularly, the active agent under consideration according to the invention is formed from the lysate of microorganisms and from all or part, in terms of amount, of the culture medium having been used for the fermentation of said bacterium and in which its cell lysis was consecutively carried out (i.e. complete fermentation medium).

From the viewpoint of the aforementioned, it emerges that the active agent formed according to the invention from the lysate and from the "complete" fermentation medium contains the cytoplasmic and cytosolic fractions, the cell wall fragments and the metabolites formed and/or released during the cell lysis of said microorganism, and all of the biological entities capable of being generated and released spontaneously by the bacterium during its fermentation process and therefore already present in the fermentation medium before the cell lysis of said bacterium.

Consequently, an active agent according to the invention, i.e. formed from a lysate of a bacterium belonging to the *Vitreoscilla* sp. genus (in particular the species: *Vitreoscilla filiformis*) in a complete fermentation medium according to the invention is clearly different than the supernatant of a fermentation medium of a bacterium belonging to the *Vitreoscilla* sp. genus (in particular the species: *Vitreoscilla filiformis*).

Indeed, the active agent under consideration according to the invention, as opposed to the supernatant, contains cell fragments of said bacterium represented by the lysate.

An active agent according to the invention, i.e. formed from a lysate of a bacterium belonging to the *Vitreoscilla* sp. genus (in particular the species: *Vitreoscilla filiformis*) in a complete fermentation medium according to the invention, is also different than the biomass or biomass fraction, or even than a lysate or lysate fraction, isolated from a fermentation medium of a bacterium belonging to the *Vitreoscilla* sp. genus (in particular the species: *Vitreoscilla filiformis*).

Indeed, the active agent under consideration according to the invention, as opposed to this biomass or biomass fraction, or this lysate or lysate fraction, contains a significant amount of water-soluble metabolites naturally released into the culture medium during the proliferation of said bacterium.

For the purposes of the present invention, the expression "nonaqueous constituents" implies that water, which is a major constituent of conventional fermentation media, is not part of the constituents that must remain as such, i.e. in equal amount, in the complete culture medium according to the invention.

Thus, the expression "complete medium" is also understood to be a form of complete medium termed concentrated owing to the fact that it is obtained at the end of a partial evaporation of the water constituting a fermentation medium in which the culturing of the corresponding microorganism and the cell lysis thereof were consecutively carried out. Of course, this evaporation is carried out under operating conditions adjusted so as not to impair the integrity of the nonaqueous constituents forming this complete medium.

Fermentation Medium Composition

By definition, a fermentation or else culture medium is a support which enables the culturing and therefore, as appropriate, the growth of cells, bacteria and yeast. In principle, the cells find in this medium the components essential for them to multiply in large number rapidly, but also sometimes elements which will make it possible to favor the growth of a specific bacterial genus or of a particular family, in this case a bacterium belonging to the *Vitreoscilla* sp. genus (in particular the species: *Vitreoscilla filiformis*).

Its composition must therefore meet the nutritive requirements of the microorganism under consideration and necessary for the proliferation thereof.

More specifically, the composition of this culture medium must:
cover the needs in terms of mineral ions and growth factors, and provide the carbon and energy source;
have a pH close to the optimum pH; and
have an optimum ionic strength (the medium may be isotonic, but this is not obligatory).

Thus, the composition of a fermentation medium suitable for the invention comprises at least:
a carbon and energy source, generally represented by sugar and advantageously glucose,
a potassium and phosphorus source, like, for example, $K_2HPO_4$,
a nitrogen and sulfur source which can be represented by the compound $(NH_4)_2SO_4$,
a magnesium source such as, for example, $MgCl_2$,
a calcium source such as, for example, $CaCl_2$,
an iron source, and more particularly iron citrate, the role of the citrate being to keep the iron in solution,
a source of trace elements chosen in particular from salts of Cu, Zn, Co, Ni, B, Ti,
a source of water, generally sterile, essential for all forms of life,
a pH buffer which can be represented by $KH_2PO_4$.

If one of these components is not present, the bacteria do not grow because they cannot by themselves compensate for its absence.

By way of illustration of a fermentation medium suitable for the growth of a microorganism in accordance with the invention, mention may particularly be made of the medium represented in example 1 hereinafter.

An effective amount of the microorganism under consideration according to the invention is introduced therein and the whole mixture is placed under conditions suitable for the proliferation of said microorganism.

To obtain a lysate of bacteria belonging to the *Vitreoscilla* sp. genus in a complete fermentation medium, according to a method comprising a step of culturing said bacteria, those skilled in the art may refer in particular to example 1.

Advantageously, to obtain an active agent according to the invention, i.e. a lysate of bacteria belonging to the *Vitreoscilla* sp. genus in a complete fermentation medium, the biomass (bacterial cells after the growth phase, present in the medium in which they were cultured) is frozen, for example at a temperature of −20° C., and then sterilized, preferably by heat, in particular by subjecting the previously frozen biomass to a step of heating at a temperature above 100° C.

By way of illustration, the biomass sterilization step can be carried out by autoclaving, for example at a temperature of 121° C.

As emerges from the aforementioned, at the end of this culturing of said microorganism, the latter is converted into lysate form directly in the fermentation medium that was used to culture it.

Lysis of Bacteria in Order to Obtain an Active Agent According to the Invention

A lysate commonly denotes a material obtained after the destruction or dissolution of biological cells via a phenomenon known as cell lysis, thus causing the release of the intracellular and cellular biological constituents naturally contained in the biological cells under consideration.

For the purposes of the present invention, the term "lysate" denotes all of the lysate obtained by lysis of the microorganism concerned, namely a bacterium belonging to the *Vitreoscilla* sp. genus (in particular of the species: *Vitreoscilla filiformis*).

The lysate used is therefore formed from all of its intracellular biological constituents, in particular its metabolites and the constituents of the cell walls and membranes generated during its cell lysis.

For the purposes of the invention, the term "metabolite" denotes any substance resulting from the metabolism of the microorganism under consideration according to the invention.

This cell lysis may be accomplished via various techniques, such as, for example, an osmotic shock, a heat shock, via ultrasonication, or alternatively under a mechanical stress of centrifugation type.

More particularly, this lysate may be obtained according to the technique described in U.S. Pat. No. 4,464,362, and in particular according to the following protocol.

The fermentation medium having been used to culture the microorganism under consideration and therefore containing said microorganism is subjected to disintegration by ultrasound in order to release therein the cytoplasmic and cytosolic fractions, the cell wall fragments and the products resulting from the metabolism of this microorganism. All these components are then preserved therein in their natural distribution in a stabilized form in the "complete" fermentation medium.

Consequently, the active agent under consideration according to the invention can be obtained via a method consisting of:
the culturing of at least one bacterium belonging to the *Vitreoscilla* sp. genus (in particular the species: *Vitreoscilla filiformis*) on a fermentation medium under conditions suitable for the proliferation of said bacterium, and
the cell lysis of said bacteria in said fermentation medium.

Bacteria Belonging to the *Vitreoscilla* sp. Genus (In Particular the species: *Vitreoscilla filiformis*)

As specified above, the microorganism under consideration according to the invention in lysate form is a nonsynthetic filamentous bacterium as defined in the classification of Bergey s Manual of Systematic Bacteriology (Vol. 3, sections 22 and 23, $9^{th}$ edition, 1989), and belonging to the *Vitreoscilla* sp. genus (in particular the species: *Vitreoscilla filiformis*).

As emerges from the examples presented hereinafter, the inventors have discovered, unexpectedly, that such a bacterium used in the form of its lysate formulated in a complete fermentation medium within the meaning of the present invention has greater properties, in terms of effectiveness, than those of the biomass obtained from the same fermentation medium.

More particularly, it is a bacterium belonging to the *Beggiatoa, Vitreoscilla, Flexithrix* or *Leucothrix* genus.

Among the bacteria that may be used, mention may be made, for example, of *Vitreoscilla filiformis* (ATCC 15551).

According to one preferred variant of the invention, it is the bacterium *Vitreoscilla filiformis*.

Applications

As previously pointed out, the active agent under consideration according to the present invention is particularly advantageous from the viewpoint of its effectiveness with regard to certain cosmetic disorders linked to dandruff conditions of the scalp, associated with a prevalence of pathogenic microorganisms on the scalp and/or an imbalance of the scalp ecoflora.

An active agent in accordance with the invention is advantageously used for the purpose of treating and/or preventing dandruff conditions and associated scalp disorders.

Thus, a scalp presenting excessive dryness or excessive secretion of sebum may manifest a dandruff condition, which, depending on the case, may be characterized by the presence of dry or oily dandruff flakes, or even pruritus and/or inflammation of the epidermis.

Dry dandruff conditions reflect a xerosis of the scalp, which may be combined with excessively rapid renewal of its stratum corneum.

Dry dandruff flakes are generally small and white or grey, and are spread over the scalp and on clothing, giving rise to an unesthetic visual effect.

As regards oily dandruff conditions, they manifest themselves in one of the subpathological forms of seborrheic dermatitis.

During dandruff conditions of the scalp, the skin barrier is imbalanced, its integrity and its moisturization are impaired and its ecoflora is disrupted. The skin of the scalp is irritated and pruriginous, fragile, less moisturized, and sensitive to infection.

As emerges from the examples hereinafter, the present invention advantageously makes it possible to have a novel active agent which is particularly effective with regard to dandruff conditions.

Advantageously, an active agent in accordance with the invention is capable of reducing the risk of occurrence of side effects.

The active agent under consideration according to the invention also advantageously makes it possible to restore a healthy scalp, in perfect homeostasis, and to re-establish a balanced ecoflora.

Consequently, the cosmetic uses, cosmetic processes and compositions according to the invention prove to be most particularly effective:

for improving the hygiene and/or care of the scalp, and in particular for preventing and/or treating dandruff conditions of the scalp, whether they are dry or oily, for preventing and/or treating disorders, in particular esthetic disorders, of the scalp associated with excessive excretion and/or secretion of sebum, for giving the scalp a feeling of well-being, for improving the comfort of the scalp, for improving and/or re-establishing the endogenous antimicrobial defences of the scalp, for preserving and/or reinforcing the integrity of the barrier functions of the scalp, for re-establishing a balanced scalp ecoflora, and/or for preventing and/or treating pruritus and itching of seborrheic origin, associated with dandruff conditions of the scalp.

Generally, the present invention is directed toward a composition comprising, as sole antidandruff active agent, a lysate of a bacterium or bacteria belonging to the *Vitreoscilla* sp. genus, in a complete fermentation medium.

However, the invention is also directed toward a composition comprising, in addition to a lysate in accordance with the invention in a complete fermentation medium, at least one distinct additional antidandruff active agent and/or at least one additional cosmetic active agent.

Additional Cosmetic Active Agent

A process according to the invention may comprise, in addition to the administration of an active agent according to the invention optionally in a form combined with an antidandruff active agent, the administration of at least one third cosmetic active agent.

Advantageously, such an additional cosmetic active agent may be intended for exerting a cosmetic, care or hygiene effect on the scalp, or even may be intended for reinforcing the skin barrier of the scalp.

It may in particular involve a probiotic microorganism, and/or a fraction thereof, and/or a metabolite thereof, which is different than said bacterium under consideration in the active agent according to the invention and/or than the complete culture of this microorganism.

Probiotic Microorganisms

For the purposes of the present invention, the term "probiotic microorganism" means a live microorganism which, when consumed in suitable amount, has a positive effect on the health of its host (Joint FAO/WHO Expert Consultation on Evaluation of Health and Nutritional Properties of Probiotic in Food Including Powder Milk with Live Lactic Acid Bacteria, 6 Oct. 2001), and which can in particular improve the intestinal microbial equilibrium.

According to one embodiment, a probiotic microorganism that is suitable for the invention may be chosen from *Lactobacillus* sp., *Bifidobacterium* sp., Cocci, yeasts and sporulated bacteria, and mixtures thereof.

According to one embodiment, a microorganism that is suitable for the invention is preferentially chosen from:

lactic acid bacteria: which produce lactic acid by fermentation of sugar. According to their morphology, they are divided into two groups:

*Lactobacillus* species: *Lactobacillus acidophilus, amylovorus, casei, rhamnosus, brevis, crispatus, delbrueckii* (subsp. *bulgaricus, lactis*), *fermentum, helveticus, gallinarum, gasseri, johnsonii, plantarum, reuteri, salivarius, alimentarius, curvatus, casei* subsp. *casei, sake,* and Cocci: *Enterococcus (faecalis, faecium), Lactococcus lactis* (subsp. *lactis* or *cremoris*), *Leuconostoc mesenteroides* subsp. *dextranicum, Pediococcus acidilactici, Sporolactobacillus inulinus, Streptococcus salvarius* subsp. *thermophilus, Streptococcus thermophilus, Staphylococcus carnosus, Staphylococcus xylosus,* bifidobacteria or *Bifidobacterium* species: *Bifidobacterium adolescentis, animalis, bifidum, breve, lactis, longum, infantis, pseudocatenulatum,* yeasts: *Saccharomyces (cerevisiae* or *boulardii),* other sporulated bacteria: *Bacillus (cereus* var. *toyo* or *subtilis), Bacillus coagulans, Bacillus licheniformis, Escherichia coli* strain *nissle, Propionibacterium freudenreichii,* and mixtures thereof.

A microorganism that is suitable for the invention may be chosen in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus* genera, and mixtures thereof.

As other examples of probiotic microorganisms that are suitable for the invention, mention may be made of *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* NCFB 1748; *Lactobacillus amylovorus, Lactobacillus casei (Shirota), Lactobacillus rhamnosus* strain GG, *Lactobacillus brevis, Lactobacillus crispatus, Lactobacillus bulgaricus, Lactobacillus delbrueckii* subsp. *lactis, Lactobacillus fermentum, Lactobacillus helveticus, Lactobacillus gallinarum, Lactobacillus gasseri, Lactobacillus johnsonii* CNCM I-1225, *Lactobacillus plantarum, Lactobacillus reuteri, Lactobacillus salivarius, Lactobacillus alimentarius, Lactobacillus curvatus, Lactobacillus casei* subsp. *casei, Lactobacillus sake, Lactococcus lactis, Enterococcus faecalis, Enterococcus faecium, Lactococcus lactis* subsp. *lactis, Lactococcus lactis* subsp. *cremoris, Leuconostoc mesenteroides* subsp. *dextranicum, Pediococcus acidilactici, Sporolactobacillus inulinus, Streptococcus salvarius* subsp. *thermophilus, Streptococcus thermophilus, Staphylococcus carnosus, Staphylococcus xylosus, Saccharomyces cerevisiae, Saccharomyces boulardii, Bacillus cereus* var. *toyo, Bacillus cereus* var. *subtilis, Bacillus coagulans, Bacillus licheniformis, Escherichia coli* strain nissle and *Propionibacterium freudenreichii*, and mixtures thereof.

More particularly, it may be a probiotic microorganism chosen from *Lactobacillus* sp., *Sporolactobacillus* sp., *Enterococcus* sp., *Lactococcus* sp., *Bacillus* sp., *Streptococcus* sp., *Pediococcus* sp., *Leuconostoc* sp. and *Bifidobacterium* sp., and in particular chosen from *Lactobacillus* sp. and *Bifidobacterium* sp., and mixtures thereof.

By way of illustration of these probiotic microorganisms, mention may be made more particularly of *Lactobacillus johnsonii, Lactobacillus reuteri, Lactobacillus rhamnosus, Lactobacillus paracasei, Lactobacillus casei, Bifidobacterium bifidum, Bifidobacterium breve, Bifidobacterium longum, Bifidobacterium animalis, Bifidobacterium lactis, Bifidobacterium infantis, Bifidobacterium adolescentis* and *Bifidobacterium pseudocatenulatum*, and mixtures thereof.

The species that are most particularly suitable are *Lactobacillus johnsonii, Lactobacillus paracasei, Bifidobacterium adolescentis* and *Bifidobacterium longum*, which were deposited, respectively, according to the Treaty of Budapest, at the Institut Pasteur (28 rue du Docteur Roux, F-75024 Paris cedex 15) on Jun. 30, 1992, Jan. 12, 1999, Apr. 15, 1999 and Apr. 15, 1999 under the following designations CNCM I-1225, CNCM I-2116, CNCM I-2168 and CNCM I-2170, and the *Bifidobacterium lactis* (Bb 12) (ATCC27536) or *Bifidobacterium longum* (BB536) genus. The strain of *Bifidobacterium lactis* (ATCC27536) may be obtained from Hansen (Chr. Hansen A/S, 10-12 Boege Alle, P.O. Box 407, DK-2970 Hoersholm, Denmark).

Advantageously, a microorganism that is suitable for the invention, as secondary active agent, may be a lactic acid probiotic microorganism.

According to one preferred embodiment, a probiotic microorganism that is suitable for the invention may in particular be a microorganism of the *Lactobacillus* sp. genus.

Preferably, a microorganism of the *Lactobacillus* sp. genus that is suitable for the invention may be chosen from the species *Lactobacillus johnsonii, Lactobacillus reuteri, Lactobacillus paracasei* and *Lactobacillus casei*, and mixtures thereof.

According to one preferred embodiment, a microorganism that is suitable for the invention may be a *Lactobacillus paracasei*.

A microorganism that is suitable for the invention may in particular be the strain *Lactobacillus paracasei* ST11 deposited according to the Treaty of Budapest, at the Institut Pasteur (28 rue du Docteur Roux, F-75024 Paris cedex 15) on Jan. 12, 1999 under the designation CNCM I-2116, and/or a fraction thereof and/or a metabolite thereof.

According to another preferred embodiment, a probiotic microorganism that is suitable for the invention may in particular be a microorganism of the *Bifidobacterium* sp. genus, and in particular *Bifidobacterium longum*, in particular *Bifidobacterium longum* (BB536).

Such a microorganism may be formulated in a composition in a proportion of at least 0.0001% expressed as dry weight, in particular in a proportion from 0.0001% to 20% and more particularly in a proportion from 0.001% to 15% by weight, in particular from 0.01% to 10% by weight and especially from 0.1% to 2% by weight relative to the total weight of the composition containing it.

Galenical Formulation

A composition containing the active agent according to the invention can be administered orally or topically.

A composition according to the invention advantageously comprises an amount of lysate of a bacterium or bacteria belonging to the *Vitreoscilla* sp. genus in a complete fermentation medium ranging from 0.001% to 10% by weight, relative to the total weight of dry extract of said composition. In certain embodiments, a composition according to the invention advantageously comprises an amount of lysate of a bacterium or bacteria belonging to the *Vitreoscilla* sp. genus in a complete fermentation medium ranging from 0.01% to 5% by weight relative to the total weight of dry extract of said composition. In other embodiments, a composition according to the invention advantageously comprises an amount of lysate of a bacterium or bacteria belonging to the *Vitreoscilla* sp. genus, in a complete fermentation medium, ranging from 0.1% to 1% by weight relative to the total weight of dry extract of said composition.

It can therefore be in any of the galenical forms normally available for the selected mode of administration.

The support may be of diverse nature depending on the type of composition under consideration.

As more particularly regards the compositions intended for external topical application, they may be aqueous, aqueous-alcoholic or oily solutions, solutions or dispersions of the lotion or serum type, emulsions of liquid or semi-liquid consistency of the milk type, obtained by dispersing a fatty phase in an aqueous phase (O/W) or conversely (W/O), or suspensions or emulsions, of soft, semi-solid or solid consistency, of the cream type, aqueous or anhydrous gels, microemulsions, microcapsules, microparticles, or vesicular dispersions of ionic and/or nonionic type.

These compositions are prepared according to the usual methods.

These compositions may in particular constitute cleansing, protective, medicated or care creams, scalp care lotions, gels or mousses, for instance scalp cleansing or disinfecting lotions.

They may also be used for the scalp in the form of solutions, creams, gels, emulsions or mousses, or alternatively in the form of aerosol compositions also containing a pressurized propellant.

A composition for topical application according to the invention may advantageously be formulated in any galenical form that is suitable for haircare, in particular in the form of a hair lotion, a shampoo, in particular an antidandruff shampoo, a hair conditioner, a disentangler, a hair cream or gel, a styling lacquer, a hairsetting lotion, a treating lotion, a dye composition (in particular for oxidation dyeing) optionally in the form of a coloring shampoo, a hair-restructuring lotion, a permanent-waving composition, a lotion or gel for combating hair loss, an antiparasitic shampoo, a medicated shampoo, in particular an anti-seborrheic shampoo, or a scalp care product, which is in particular anti-irritant, anti-ageing or restructuring, or which activates the blood circulation.

When a composition of the invention is an emulsion, the proportion of the fatty phase may range from 5% to 80% by weight and preferably from 10% to 50% by weight relative to the total weight of the composition. The oils, emulsifiers and co-emulsifiers used in the composition in emulsion form are chosen from those conventionally used in the cosmetics and/or dermatology field. The emulsifier and the co-emulsifier may be present in the composition in a proportion ranging from 0.3% to 30% by weight and preferably from 0.5% to 20% by weight relative to the total weight of the composition.

When the composition of the invention is an oily solution or gel, the fatty phase may represent more than 90% of the total weight of the composition.

In a known manner, the galenical forms intended for topical administration may also contain adjuvants that are customary in the cosmetics, pharmaceutical and/or dermatology field, such as hydrophilic or lipophilic gelling agents, hydrophilic or lipophilic active agents, preserving agents, antioxidants, solvents, fragrances, fillers, screening agents, odor absorbers and colorants. The amounts of these various adjuvants are those conventionally used in the field under consideration, for example from 0.01% to 20% of the total weight of the composition. Depending on their nature, these adjuvants may be introduced into the fatty phase and/or into the aqueous phase.

As fatty substances that may be used in the invention, mention may be made of mineral oils, for instance hydrogenated polyisobutene and liquid petroleum jelly, plant oils, for instance a liquid fraction of shea butter, sunflower oil and apricot kernel oil, animal oils, for instance perhydrosqualene, synthetic oils, in particular purcellin oil, isopropyl myristate and ethylhexyl palmitate, unsaturated fatty acids and fluoro oils, for instance perfluoropolyethers. It is also possible to use fatty alcohols, fatty acids, for instance stearic acid and, for example, waxes, in particular paraffin wax, carnauba wax and beeswax. It is also possible to use silicone compounds, for instance silicone oils and for example cyclomethicone and dimethicone, and silicone waxes, resins and gums.

As emulsifiers that may be used in the invention, mention may be made, for example, of glyceryl stearate, polysorbate 60, the mixture of cetylstearyl alcohol/cetylstearyl alcohol oxyethylenated with 33 mol of ethylene oxide sold under the name Sinnowax AO® by the company Henkel, the mixture of PEG-6/PEG-32/glycol stearate sold under the name Tefose® 63 by the company Gattefosse, PPG-3 myristyl ether, silicone emulsifiers such as cetyl dimethicone copolyol, and sorbitan monostearate or tristearate, PEG-40 stearate and oxyethylenated (20 OE) sorbitan monostearate.

As solvents that may be used in the invention, mention may be made of lower alcohols, in particular ethanol and isopropanol, and propylene glycol.

The composition of the invention may also advantageously contain a spring and/or mineral water, chosen in particular from Vittel water, waters from the Vichy Basin, and la Roche Posay water.

Hydrophilic gelling agents that may be mentioned include carboxylic polymers such as carbomer, acrylic copolymers such as acrylate/alkyl acrylate copolymers, polyacrylamides and in particular the mixture of polyacrylamide, C13-14 isoparaffin and laureth-7 sold under the name Sepigel 305® by the company SEPPIC, polysaccharides, for instance cellulose derivatives such as hydroxyalkyl celluloses and in particular hydroxypropyl cellulose and hydroxyethyl cellulose, natural gums such as guar gum, locust bean gum and xanthan gum, and clays.

Lipophilic gelling agents that may be mentioned include modified clays, for instance bentones, metal salts of fatty acids, for instance aluminum stearates and hydrophobic silica, or else ethylcellulose and polyethylene.

Cosmetic Treatment Process

As indicated previously, a process according to the invention can be carried out, topically, in particular by application to the scalp of at least one lysate of a bacterium belonging to the *Vitreoscilla* sp. genus (in particular the species: *Vitreoscilla filiformis*), in a complete fermentation medium, as an active agent for preventing and/or treating dandruff conditions of the scalp, in particular dandruff conditions associated with a proliferation of pathogenic microorganisms on the scalp and/or an imbalance of the scalp ecoflora, and more particularly of a cosmetic composition as previously defined.

Advantageously, a process of the invention via topical application can comprise the application of a composition in accordance with the invention, for example in the form of cleansing creams, scalp treatment or care lotions or gels, scalp care gels or mousses, for instance cleansing or disinfecting lotions, or shampoos. According to one implementation variant, the process of the invention can comprise the topical application to the scalp of at least one active agent according to the invention, for example in the form of a shampoo, gels, sera or lotions.

A topical cosmetic process according to the invention can be carried out on a daily basis for example, at a rate of, for example, a single administration per day or one administration twice a day, for example once in the morning and once in the evening.

A topical cosmetic process according to the invention can be carried out over a time period ranging from one week to several weeks, or even several months, this period moreover possibly being repeated after periods without treatment, for several months or even several years.

By way of example, the topical administration of a compound according to the invention may be repeated, for example, 2 to 3 times a week or more and generally over an extended period of at least 4 weeks, or even 4 to 15 weeks, with, where appropriate, one or more periods of interruption.

In the description and the examples that follow, unless otherwise indicated, the percentages are weight percentages and the ranges of values written in the form "between . . . and . . . " include the stated lower and upper limits.

The examples hereinafter are presented as nonlimiting illustrations of the field of the invention.

EXAMPLES

Example 1

Preparation of an Active Agent in Accordance with the Invention

The complete fermentation medium is prepared by means of a culture of the *Vitreoscilla filiformis* strain, in its complete culture medium.

The initial culture medium for obtaining the complete fermentation medium has the composition described in table 1 below.

TABLE 1

| Chemical name | [c] |
| --- | --- |
| Autolytic extract of yeast | 4 g/l |
| Soybean papainic peptone F | 3 g/l |
| Glucose - Roferose | 3 g/l |
| $KH_2PO_4$ | 0.088 g/l |
| $CaCl_2$ | 0.050 g/l |
| $CuSO_4 \cdot 5H_2O$ | 60 µg/l |
| $MnSO_4 \cdot 1H_2O$ | 152 µg/l |
| KI | 20 µg/l |
| $ZnSO_4 \cdot 7H_2O$ | 200 µg/l |
| $AlCl_3 \cdot 6H_2O$ | 100 µg/l |
| osmosed water | qs 1 l |

In order to obtain a cosmetic active agent according to the invention, i.e., in this example, a lysate of *Vitreoscilla filiformis* bacteria in a complete fermentation medium, the process as described hereinafter was carried out.

The *Vitreoscilla filiformis* strain was obtained from the ATCC (strain 15551). This strain is cultured in a particular culture medium, 2BHG2, the composition of which is given above.

The biomass is obtained by continuous culture in a bioreactor with a working capacity of 3000 liters. A growth rate of approximately 70% of the µmax (µ=0.12 H-1) is recorded during the continuous production phase. During this step, the pH (7.00), the temperature (26° C.) and the dissolved oxygen (0.5%) are controlled. The extraction and the separation of the cells is obtained by centrifugation (10 000 g/20 min). The biomass is frozen at −20° C. and is then packaged in pouches (breaking of sterility) and is stabilized by sterilization at 121° C. for 30 min. The biomass is then known as Vfe.

The biomass specification analyses are the following:
Fixed residue at 105° C. (g/100 g): 4.0 to 4.5%
total nitrogen content with respect to AM: 10.0 to 14.0%
Microbiology: 0 microorganism/g
3-hydroxybutyric acid content: 2 to 10 g/l (<10 g/l)
pH of the solution as it is: 4 to 5.

The fermentation medium is the complete culture, obtained during the continuous fermentation. The glucose in the starting medium was consumed by the microorganisms (micro-controlled by the carbon source), as were various elements of the peptones and yeast extract provided at the start. The fermentation medium currently tested is taken directly from the fermenter, and then undergoes the sterilization scheme.

The FM, which is the unconcentrated complete culture (0.7 to 0.9% of DM), is autoclaved (30 min, 121° C.), as is the lysate (4.0 to 4.5% of DM).

In the examples which follow, the active agent according to the invention (the lysate of *Vitreoscilla filiformis* bacteria in a complete fermentation medium, also denoted "FM") and also a comparative active agent constituted of the isolated bacterial lysate in the absence of the complete fermentation medium were the subject of clinical tests on heads in order to verify their antidandruff activities, in comparison with a reference antidandruff shampoo formulation. Two reference antidandruff shampoo formulations were in particular tested, respectively a first reference shampoo formulation comprising octopirox and a second reference shampoo formulation comprising ZnPT.

Example 2

In example 2, the effects, on the dandruff conditions of the scalp, of (i) a shampoo formulation comprising an antidandruff active agent according to the invention (lysate of *Vitreoscilla filiformis* bacteria in a complete fermentation medium, prepared in accordance with example 1) and (ii) a reference antidandruff shampoo formulation free of the antidandruff active agent according to the invention, comprising a conventional antidandruff active agent (ZnPT), were compared.

The lysate of bacteria in a complete fermentation medium (antidandruff active agent according to the invention) as obtained in example 1 is therefore used as antidandruff active agent in a shampoo formulation, the basic composition of which is described in table 2 below.

Figure 2:
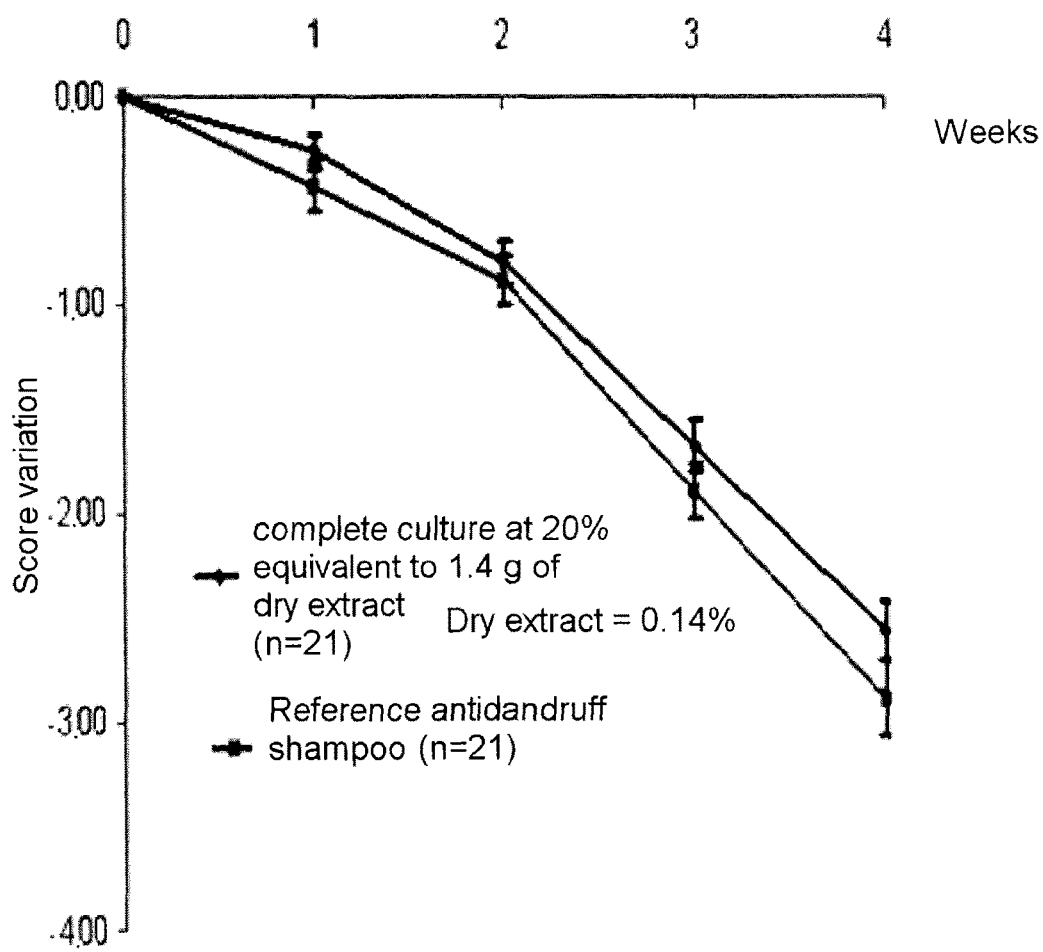
FIG. 2 shows the results of the comparison of the effects on the dandruff of (i) a shampoo comprising the active agent of the invention at 20% by weight (corresponding to 0.14% of dry extract), and (ii) the reference shampoo formula.

Several clinical studies were carried out,
a clinical study 1, corresponding to FIG. 1,
a clinical study 2, corresponding to FIG. 2,
a clinical study 3, corresponding to FIGS. 3 to 11.

TABLE 2

| | Ingredients | | Concentration (% by weight |
| --- | --- | --- | --- |
| Chemical name | INCI Name (US) | INCI name (EU) | relative to the total weight) |
| Lysate of *Vitreoscilla filimormis* in their complete medium (complete culture at 160 g/l) | | | 2 |
| Sodium lauryl ether sulfate (2.2 OE) as an aqueous solution | Sodium laureth sulfate | Sodium laureth sulfate | 20.1 |
| Cocoylamidopropyl betaine as an aqueous solution | Cocamidopropyl betaine | Cocamidopropyl betaine | 6.3 |
| Water | | | qs |

The shampoo formulation, used in clinical study 3, of table 2 comprises 2% by weight of the antidandruff active agent according to the invention (lysate of bacteria in a complete fermentation medium, at a concentration of 160 g/l) relative to the total weight of the composition, i.e. 0.32% by weight of said antidandruff active agent, relative to the total weight of dry extract of said composition.

In an equivalent manner, the shampoo formulation used in clinical study 3 comprises 1% by weight of the antidandruff active agent according to the invention (lysate of bacteria in a complete fermentation medium, at a concentration of 160 g/l) relative to the total weight of the composition, i.e. 0.16% by weight of said antidandruff active agent, relative to the total weight of dry extract of said composition.

In an equivalent manner, the shampoo formulation used in clinical study 1 comprises 2.5% and 5% by weight of the bacterial lysate active agent (lysate of bacteria free of the complete fermentation medium) relative to the total weight of the composition, i.e., respectively, 0.1075% and 0.215% by weight of said active agent, relative to the total weight of dry extract of said composition.

In an equivalent manner, the shampoo formulation used in clinical study 2 comprises 20% by weight of the antidandruff active agent according to the invention (lysate of bacteria in a complete fermentation medium, at a concentration of 7.5 g/l) relative to the total weight of the composition, i.e. 0.14% by weight of said antidandruff active agent, relative to the total weight of dry extract of said composition.

It is specified that the amount as % by weight of the lysate in its complete fermentation medium ranges from 0.1% to 0.5% on a dry extract basis.

By way of comparison, the reference shampoo formulation described in table 3 below, which comprises the zinc pyrithione (ZnPT) antidandruff active agent present at 2% by weight, relative to the total weight of the composition, i.e. 1% of dry extract by weight of zinc pyrithione, relative to the total weight of dry extract of said composition, was tested.

TABLE 3

| Ingredients | | | Concentration (% by weight |
|---|---|---|---|
| Chemical name | INCI Name (US) | INCI name (EU) | relative to the total weight) |
| Zinc pyrithione as an aqueous dispersion | Zinc pyrithione | Zinc pyrithione | 2.083, which corresponds to a dry extract by weight of 1% |
| Sodium lauryl ether sulfate (2.2 OE) as an aqueous solution | Sodium laureth sulfate | Sodium laureth sulfate | 20.1 |
| Cocoylamidopropyl betaine as an aqueous solution | Cocamido-propyl betaine | Cocamido-propyl betaine | 6.3 |
| Water | | | qs |

Protocol

The treatment consists in topically applying the formula tested for four weeks.

Clinical Study 1:

This study was carried out in order to compare (i) a shampoo comprising an isolated bacterial lysate, free of complete fermentation medium, used at 2.5% by weight (corresponding to 0.1075% of dry extract), (ii) a shampoo comprising an isolated bacterial lysate, free of complete fermentation medium, used at 5% by weight (corresponding to 0.215% of dry extract), and (iii) the reference antidandruff shampoo formula.

This study was performed on 60 adult male subjects aged between 18 and 60, who were identified following a clinical evaluation of their dandruff condition, classified from moderate to severe, with scores of greater than or equal to 5 (on a scale from 0 to 9) in the presence of squamae adhering to at least two quarters of the head, and of their scalp erythema.

The 60 subjects were divided up into 3 parallel groups of 20 subjects, with each of the groups being treated with just one of the two compositions+a control group.

Clinical Study 2:

This study was carried out in order to compare (i) a shampoo comprising the active agent of the invention at 20% by weight (corresponding to 0.14% of dry extract), and (ii) the reference shampoo formula. The active agent of the invention is in a form at 7.5 g/l.

This study was performed on 42 adult male subjects aged between 18 and 60, who were identified following a clinical evaluation of their dandruff condition, classified from moderate to severe, with scores of greater than or equal to 5 (on a scale from 0 to 9) in the presence of squamae adhering to at least two quarters of the head, and of their scalp erythema.

The 42 subjects were divided up into 2 parallel groups of 21 subjects, with one group being treated with a composition having the active agent of the invention+one control group with the reference antidandruff active agent.

Clinical Study 3:

This study was carried out in order to compare (i) a shampoo comprising the active agent of the invention at 0.16% on a dry extract basis, (ii) a shampoo comprising the active agent of the invention at 0.32% on a dry extract basis, and (iii) the reference shampoo formula, comprising zinc pyrithione at 1% on a dry extract basis. The active agent of the invention is in a form at 160 g/l.

This study was performed on 67 adult male subjects aged between 18 and 60, who were identified following a clinical evaluation of their dandruff condition, classified from moderate to severe, with scores of greater than or equal to 5 (on a scale from 0 to 9) in the presence of squamae adhering to at least two quarters of the head, and of their scalp erythema.

The 67 subjects were divided up into 3 parallel groups of 22 subjects, with each of the groups being treated with just one of the two compositions+a control group.

Clinical Evaluation of the Dandruff Condition of the Scalp (Scores)

The effects on the dandruff were tested and assessed by comparing the groups on D2, D7, D15, D21 and D28 through clinical evaluations carried out with respect to the following parameters: free dandruff flakes, adherent squamae and erythema, and the overall score was calculated.

These evaluations were performed by qualified dermatologists according to the techniques usually used in the field.

At each visit, the dandruff condition, free dandruff flakes and adherent squamae were scored, for each item, by the investigator using a scale of 0-9, a score of 0 being assigned in the absence of a dandruff state and a score of 9 being assigned for a very severe dandruff state.

The results are expressed by the difference between (i) the value of the score before the beginning of the treatment and (ii) the value of the score at the time of each measurement.

Self-Evaluation of the Dandruff Condition of the Scalp by the Subjects

The effects on the dandruff were tested and assessed by comparing the groups on D2, D7, D15, D21 and D28 through clinical self-evaluations carried out on the subjects themselves. These self-evaluations represent "the Opinion of the subjects".

The results are expressed by the value of the dandruff score assigned by the subject himself.

Clinical Evaluation of Itching of the Scalp

The effects on itching of the scalp were tested and assessed by comparing the groups on D2, D7, D15, D21 and D28 through clinical evaluations carried out according to a conventional protocol.

These evaluations were performed by qualified dermatologists according to the techniques usually used in the field.

At each visit, the itching of the scalp was scored by the investigator using a scale of 0-9, a score of 0 being assigned in the absence of itching and a score of 9 being assigned in the presence of very severe itching.

The results are expressed by the difference between (i) the value of the score before the beginning of the treatment and (ii) the value of the score at the time of each measurement.

Results

The results obtained are shown in FIGS. 1 to 4.

FIG. 1 shows the results of the comparison of the effects on the dandruff of (i) a shampoo comprising an isolated bacterial lysate, free of complete fermentation medium, used at 2.5% by weight (corresponding to 0.1075% of dry extract), (ii) a shampoo comprising an isolated bacterial lysate, free of complete fermentation medium, used at 5% by weight (corresponding to 0.215% of dry extract), and (iii) the reference antidandruff shampoo formula.

It emerges from the comparison of the results of FIG. 1 that the two shampoo formulations comprising an isolated bacterial lysate, used at 0.1075% and 0.215% on a dry extract basis, each give an overall score which is significantly lower than the overall score obtained with the reference shampoo formulation. Consequently, the results of FIG. 1 show that the shampoo formulations comprising an isolated bacterial lysate, free of the fermentation medium, exert a very weak, and even virtually zero, antidandruff effect, in comparison with the reference shampoo formula.

FIG. 2 shows the results of the comparison of the effects on the dandruff of (i) a shampoo comprising the active agent of the invention at 20% by weight (corresponding to 0.14% of dry extract), and (ii) the reference shampoo formula.

The results of FIG. 2 show that the shampoo formulation in accordance with the invention exhibits an antidandruff activity which is equivalent to that of the reference formula, this being the case at a dry extract equivalent of 0.14%, i.e. at a concentration of active agent for which a weak effect or no effect is observed with the comparative shampoo formulations comprising an isolated bacterial lysate, free of complete fermentation medium (see the results of FIG. 1).

Figure 3:
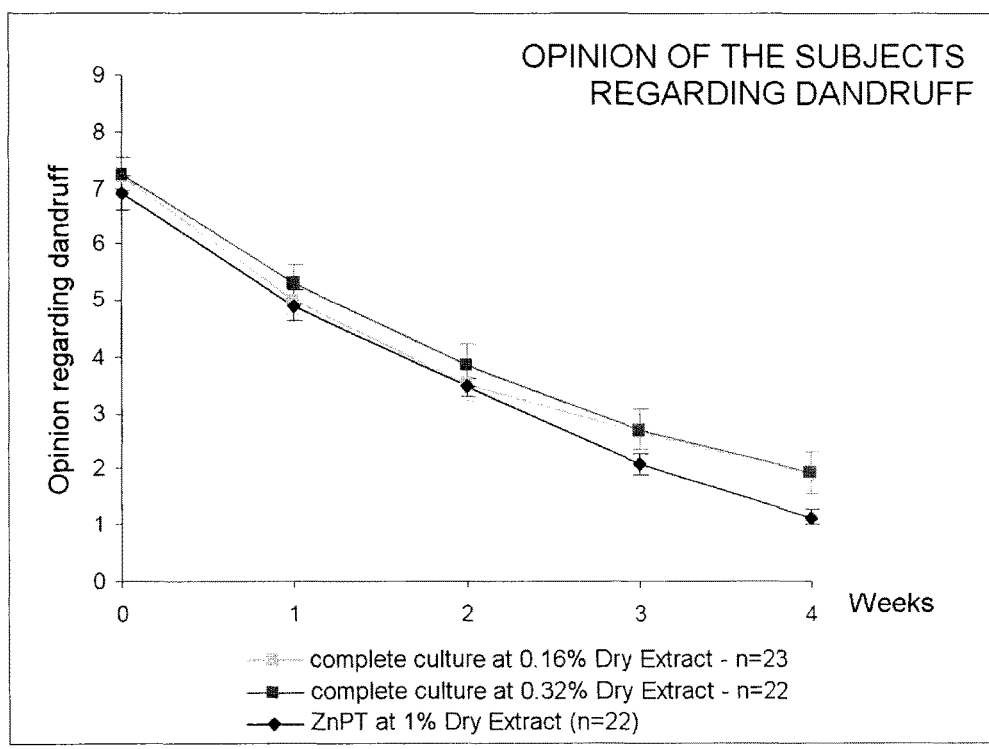
FIG. 3 shows the results of the comparison of the effects on the dandruff of (i) a shampoo comprising the active agent of the invention at 0.16% on a dry extract basis, (n) a shampoo comprising the active agent of the invention at 0.32% on a dry extract basis, and (iii) the reference shampoo formula, comprising zinc pyrithione at 1% on a dry extract basis.

FIG. 3 shows the results of the comparison of the effects on the dandruff of (i) a shampoo comprising the active agent of the invention at 0.16% on a dry extract basis, (ii) a shampoo comprising the active agent of the invention at 0.32% on a dry extract basis, and (iii) the reference shampoo formula, comprising zinc pyrithione at 1% on a dry extract basis.

The results of FIG. 3 shows that a shampoo formulation comprising 0.16% on a dry extract basis of active agent according to the invention produces an antidandruff effect which is equivalent to the reference shampoo formulation which comprises 1% by weight of conventional active agent (see also statistical study of EXAMPLE 6).

Figure 4:
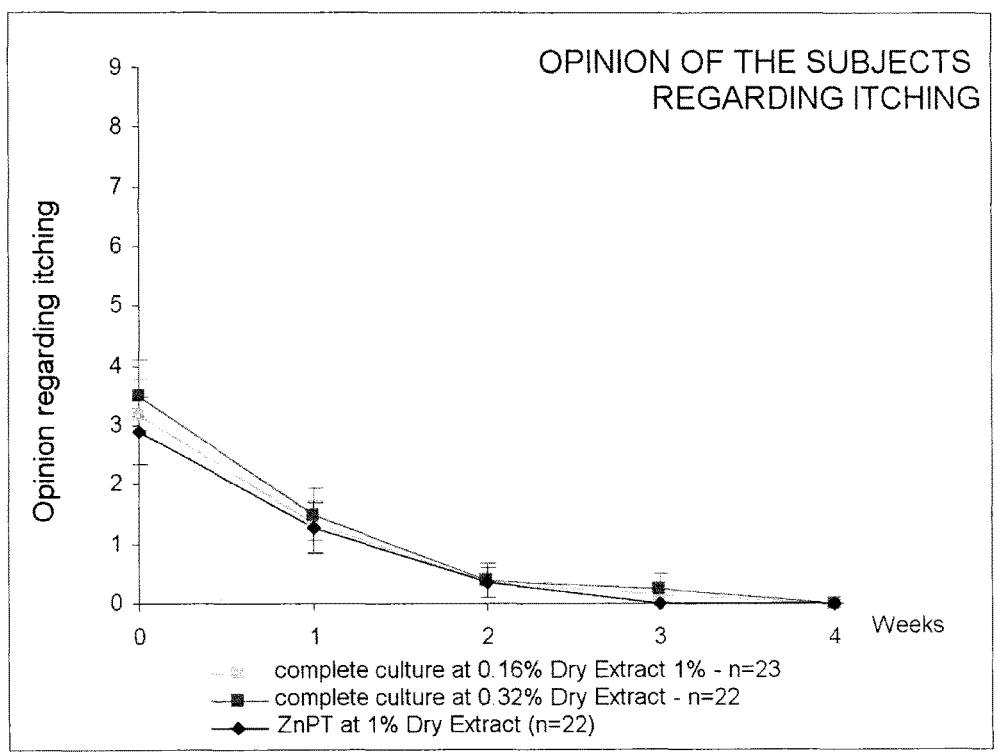
FIG. 4 shows the results of the comparison of the effects on the itching of the scalp of (i) a shampoo comprising the active agent of the invention at 0.16% on a dry extract basis, (ii) a shampoo comprising the active agent of the invention at 0.32% on a dry extract basis, and (iii) the reference shampoo formula, comprising zinc pyrithione at 1% by weight.

FIG. 4 shows the results of the comparison of the effects on the itching of the scalp of (i) a shampoo comprising the active agent of the invention at 0.16% on a dry extract basis, (ii) a shampoo comprising the active agent of the invention at 0.32% on a dry extract basis, and (iii) the reference shampoo formula, comprising zinc pyrithione at 1% by weight.

The results of FIG. 4 show that a shampoo formulation comprising 0.16% and 0.32% on a dry extract basis of active agent according to the invention produces an effect against itching of the scalp which is equivalent to the reference shampoo formulation which comprises 1% by weight of conventional active agent.

Example 3

Negative MIC Data for Showing that the Effect is not Antifungal

The test product is brought into contact with the *Malassezia* suspension. The mixture is deposited at the surface of agar medium. It is spread and the excess is recovered before incubation. It is incubated for at least 5 days at 30° C.

The products are placed in solution in liquid modified Leeming and Notman medium (LNm) and the tests are carried out in duplicate. The complete culture is at 7.5 g/l or 150 g/l (concentrated version) on a dry matter basis.

The complete culture was tested at 10% (for the concentration at 7.5 g/l) and at 1% (for the concentration at 150 g/l).

The positive reference is 1% zinc pyrithione.

The solutions of the products are twice as concentrated in order to take into account the dilution to ½ during the bringing into contact with the *Malassezia* suspension.

TABLE 8

| Strain | OD550 nm | Concentrations cfu/ml |
|---|---|---|
| *Malassezia globosa* CBS 7708 | 1.369 | 7500 |
| *Malassezia restricta* CBS 7708 | 1.137 | 600 |

The *Malassezia globosa* and *restricta* strains were received on agar slopes and were subcultured and incubated at 30° C. until the tests.

The suspensions are prepared in 15 ml of a buffered solution (ref AEB611294, AES).

The density of the suspensions is taken at 550 nm.

The antifungal effect of the reference product is evaluated via the absence of growth of the *Malassezia* strain tested. This inhibition is evaluated relative to the growth control.

The inhibitions are scored from 3 to 0 via assessment of the density of the culture at the surface of the agar, in comparison with the growth control for the strain.

TABLE 9

| SCORE | INTERPRETATION |
|---|---|
| 3 | No growth |
| 2 | Growth < in the control dish |
| 1 | Growth < in the control dish |
| 0 | Growth comparable to the control dish |

TABLE 10

| | *Malassezia restricta* | | *Malassezia globosa* | |
|---|---|---|---|---|
| Growth control | Culture spread out suitable density | | Culture spread out suitable density | |
| Zinc pyrithione control | 3 Total inhibition | | 3 Total inhibition | |
| TESTS (Duplicate) | B1 | B2 | B1 | B2 |
| 50% 0.1M TRIS control | 0 | 0 | 0 | 0 |
| Complete culture at 10% (concentration 7.5 g/l) i.e. a dry extract = 0.075% | 0 | 0 | 0 | 0 |
| Complete culture at 1% (concentration 150 g/l) i.e. a dry extract = 0.15% | 0 | 0 | 0 | 0 |

The products do not exhibit any antifungal inhibition on *Malassezia restricta* or *Malassezia globosa*.

Example 4

Effect on the Dandruff Condition: Opinion with Regard to the Overall Dandruff Score and Regarding the Opinion of the Subjects with Regard to Dandruff In this example, the antidandruff effect of a shampoo formulation in accordance with the invention was evaluated in comparison with the reference shampoo formulation (comprising the zinc pyrithione active agent).

The lysate of *Vitreoscilla filiformis* bacteria in the complete fermentation medium was used in an evapoconcentrated form, at concentrations on a dry extract basis of the lysate of 0.16% and 0.32% dry extract.

Clinical Evaluation of the Dandruff Condition of the Scalp (Scores)

The effects on the dandruff were tested and assessed by comparing the groups on D0, D7, D15, D21 and D28 through clinical evaluations carried out with respect to the following parameters: free dandruff flakes, adherent squamae and erythema, and the overall score was calculated.

These evaluations were performed by qualified dermatologists according to the techniques usually used in the field.

At each visit, the dandruff condition, free dandruff flakes and adherent squamae were scored, for each item, by the investigator using a scale of 0-9, a score of 0 being assigned in the absence of a dandruff state and a score of 9 being assigned for a very severe dandruff state.

The subjects of the various groups were also asked to carry out self-evaluations. These self-evaluations are reported as "Opinion of the subjects".

The results are given in FIGS. 5 to 9.

In FIGS. 5, 6, 8 and 9, the results are expressed in absolute values of the score at each measurement.

Figure 7:
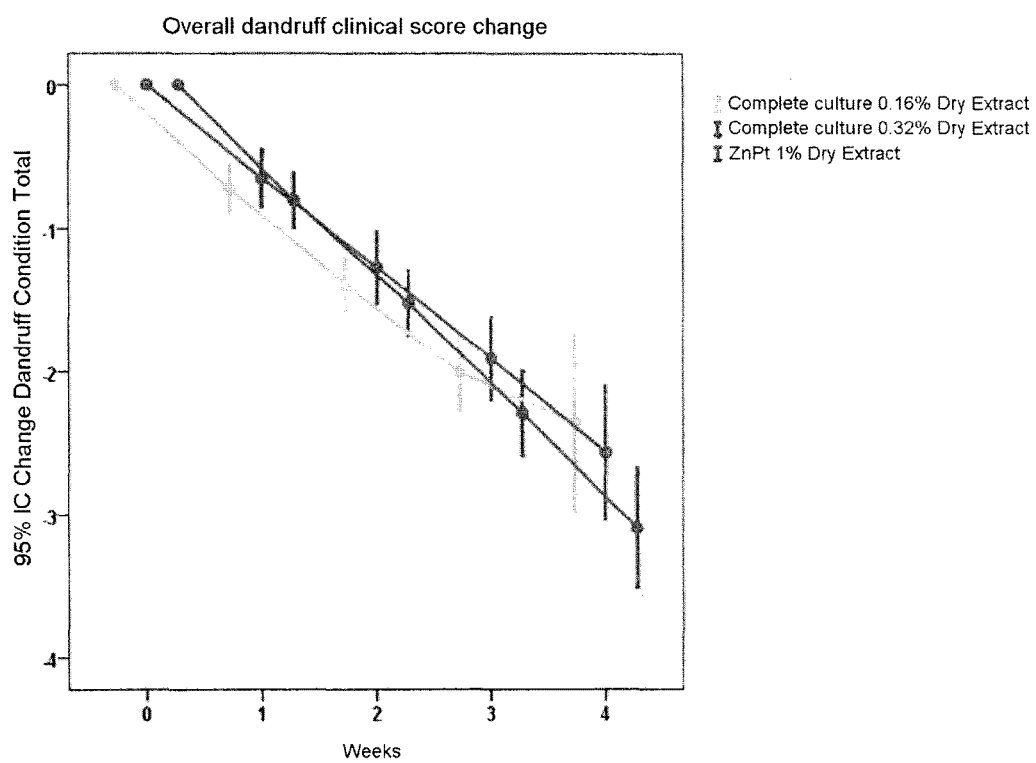
FIG. 7 shows the comparative results of the differences in overall score, obtained (i) using a shampoo formulation in accordance with the invention comprising 0.16% by weight of the active agent (bacterial lysate in the complete fermentation medium), relative to the total weight of the dry extract of the formulation, and (ii) using a shampoo formulation in accordance with the invention comprising 0.32% by weight of the active agent (bacterial lysate in the complete fermentation medium), relative to the total weight of the dry extract of the formulation.

In FIG. 7, the results are expressed by the difference between (i) the value of the score before the beginning of the treatment and (ii) the value of the score at the time of each measurement.

Figure 5:
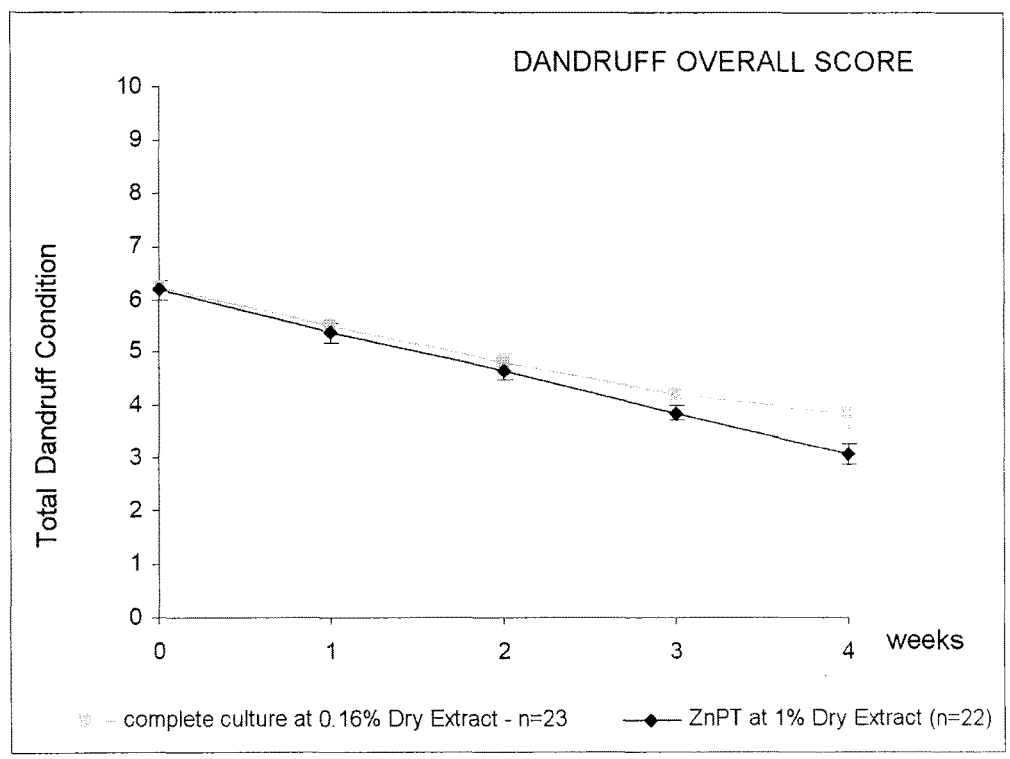
FIG. 5 shows the comparative overall score results obtained using a shampoo formulation in accordance with the invention comprising 0.16% by weight of the active agent (bacterial lysate in the complete fermentation medium), relative to the total weight of the dry extract of the formulation.

FIG. 5 shows the comparative overall score results obtained using a shampoo formulation in accordance with the invention comprising 0.16% by weight of the active agent (bacterial lysate in the complete fermentation medium), relative to the total weight of the dry extract of the formulation. The reference comparative formulation comprises 1% by weight of ZnPT active agent, relative to the total weight of the dry extract.

Figure 6:
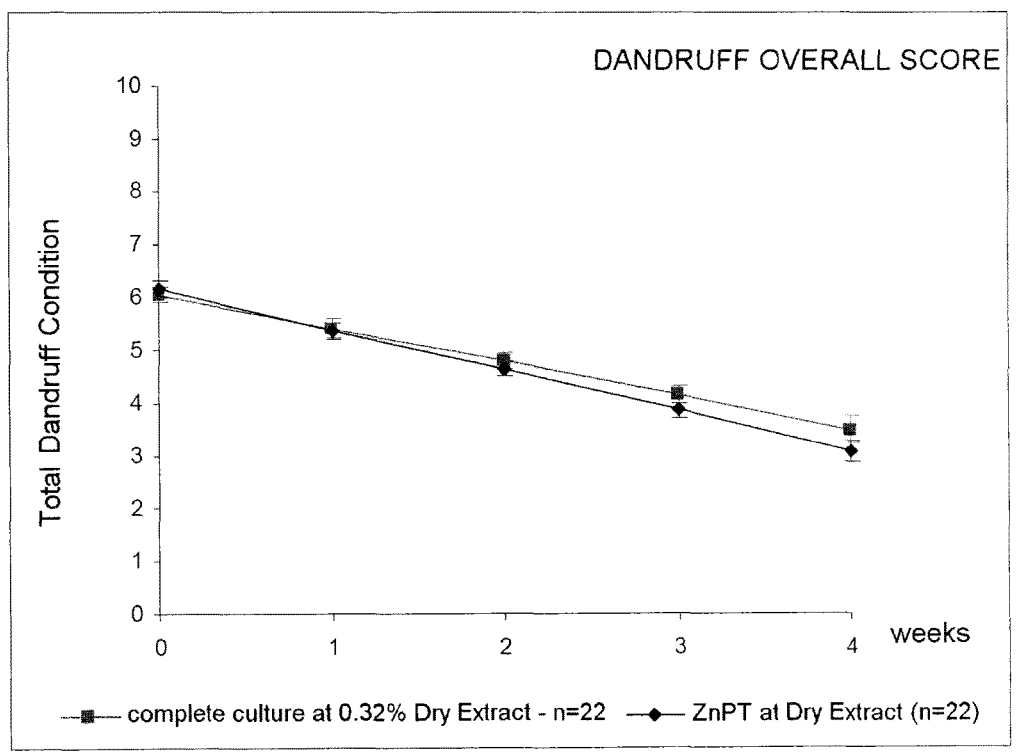
FIG. 6 shows the comparative overall score results obtained using a shampoo formulation in accordance with the invention comprising 0.32% by weight of the active agent (bacterial lysate in the complete fermentation medium), relative to the total weight of the dry extract of the formulation.

FIG. 6 shows the comparative overall score results obtained using a shampoo formulation in accordance with the invention comprising 0.32% by weight of the active agent (bacterial lysate in the complete fermentation medium), relative to the total weight of the dry extract of the formulation. The reference comparative formulation comprises 1% by weight of ZnPT active agent, relative to the total weight of the dry extract.

Figure 8:
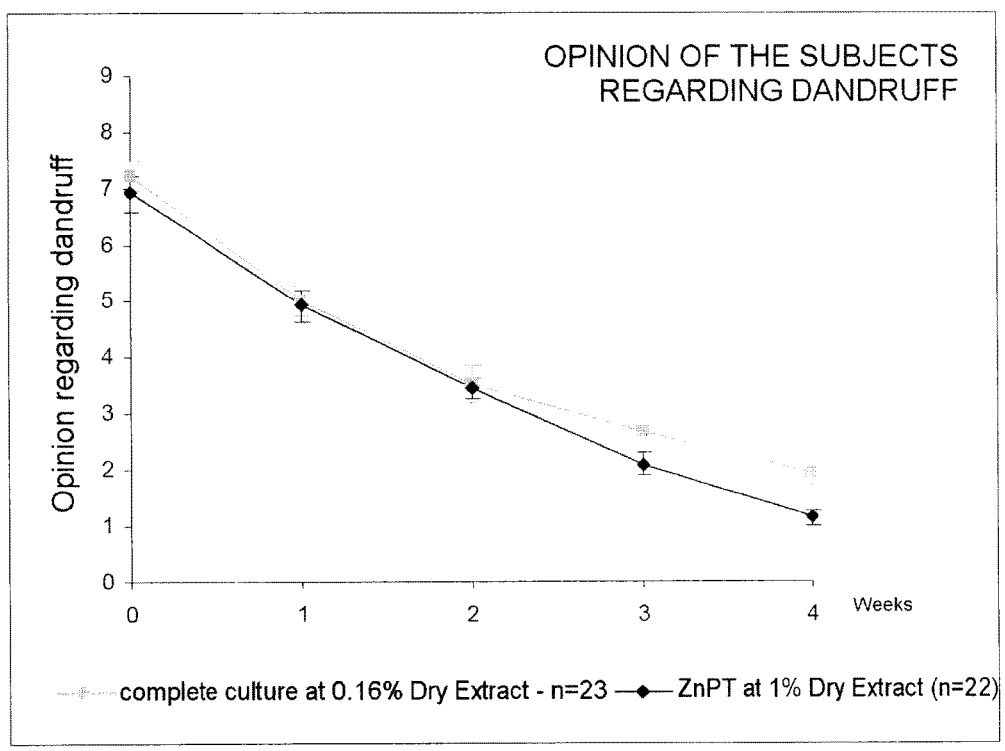
FIG. 8 shows the comparative results of the opinions of the patients treated, obtained using a shampoo formulation in accordance with the invention comprising 0.16% by weight of the active agent (bacterial lysate in the complete fermentation medium), relative to the total weight of the dry extract of the formulation.

FIG. 8 shows the comparative results of the opinions of the patients treated, obtained using a shampoo formulation in accordance with the invention comprising 0.16% by weight of the active agent (bacterial lysate in the complete fermentation medium), relative to the total weight of the dry extract of the formulation. The reference comparative formulation comprises 1% by weight of ZnPT active agent, relative to the total weight of the dry extract.

Figure 9:
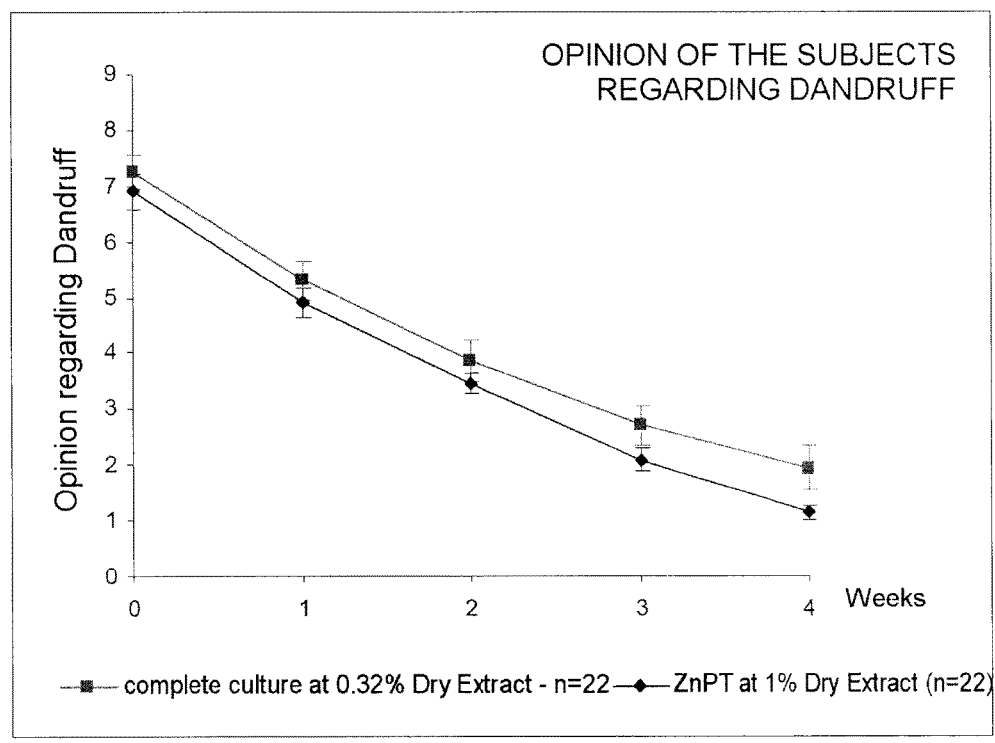
FIG. 9 shows the comparative results of the opinions of the patients treated, obtained using a shampoo formulation in accordance with the invention comprising 0.32% by weight of the active agent (bacterial lysate in the complete fermentation medium), relative to the total weight of the dry extract of the formulation.

FIG. 9 shows the comparative results of the opinions of the patients treated, obtained using a shampoo formulation in accordance with the invention comprising 0.32% by weight of the active agent (bacterial lysate in the complete fermentation medium), relative to the total weight of the dry extract of the formulation. The reference comparative formulation comprises 1% by weight of ZnPT active agent, relative to the total weight of the dry extract.

FIG. 7 shows the comparative results of the differences in overall score, obtained (i) using a shampoo formulation in accordance with the invention comprising 0.16% by weight of the active agent (bacterial lysate in the complete fermentation medium), relative to the total weight of the dry extract of the formulation, and (ii) using a shampoo formulation in accordance with the invention comprising 0.32% by weight of the active agent (bacterial lysate in the complete fermentation medium), relative to the total weight of the dry extract of the formulation. The reference comparative formulation comprises 1% by weight of active agent, relative to the total weight of the dry extract.

All of the results of example 6 show that a shampoo formulation in accordance with the invention, which comprises 0.16% of antidandruff active agent, has an activity which is at least identical to, and even slightly greater than, the reference shampoo formulation which comprises 1% of a conventional antidandruff active agent.

All of the results of example 6 show that a shampoo formulation in accordance with the invention, which comprises 0.32% of antidandruff active agent, has an activity which is at least identical to, and even slightly greater than, the reference shampoo formulation which comprises 1% of a conventional antidandruff active agent.

Statistical Analysis:

The complete culture at 0.32% dry extract is never significantly different than ZnPT at 1% dry extract.

Once adjusted to take into account the multiplicity of the tests (3 comparisons), the complete culture at 0.16% dry extract is never significantly different than ZnPT at 1% dry extract.

The two complete culture formulations at 0.32% dry extract and 0.16% dry extract are not significantly different.

Example 5

Effect on the Dandruff Condition: Opinion of the Subjects with Regard to Itching In this example, the antidandruff effect of a shampoo formulation in accordance with the invention was evaluated in comparison with the reference shampoo formulation (comprising the zinc pyrithione active agent).

The lysate of *Vitreoscilla filiformis* bacteria in the complete fermentation medium was used in an evapoconcentrated form, at concentrations on a dry extract basis of the lysate of 0.16% and 0.32% dry extract.

The effects on itching of the scalp were tested and assessed by comparing the groups on D2, D7, D15, D21 and D28 through clinical evaluations carried out according to a conventional protocol.

These evaluations were performed by qualified dermatologists according to the techniques usually used in the field.

Figure 10:
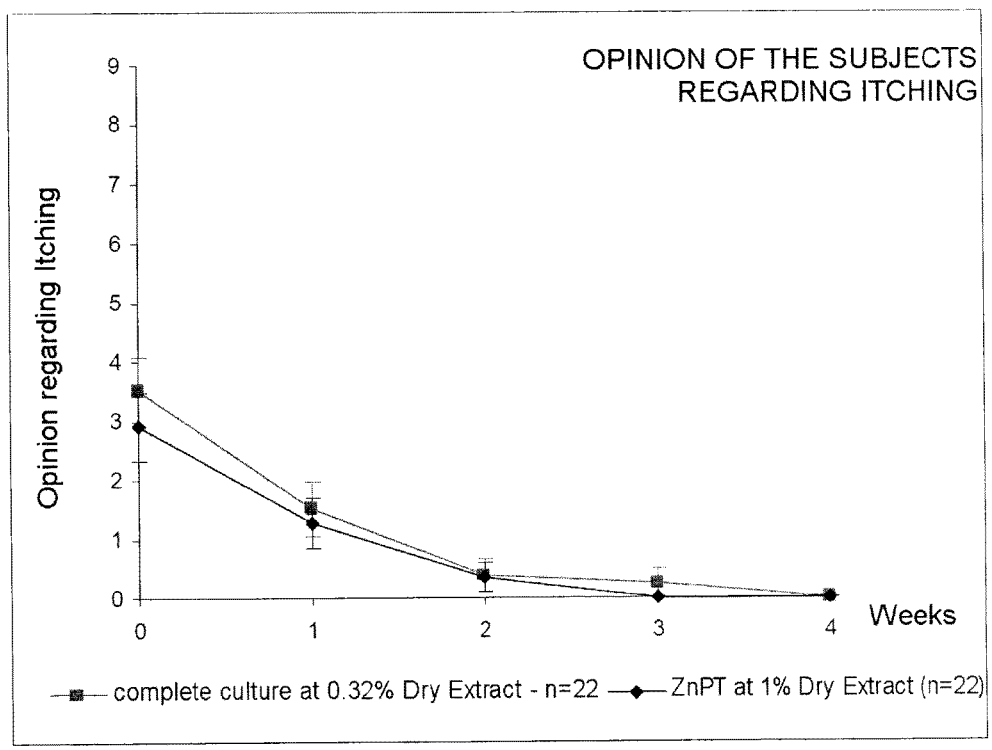
FIG. 10 shows the comparative results of effects on itching of the scalp (opinion of the subjects), obtained using a shampoo formulation in accordance with the invention comprising 0.32% by weight of the active agent (bacterial lysate in the complete fermentation medium), relative to the total weight of the dry extract of the formulation.
Figure 11:
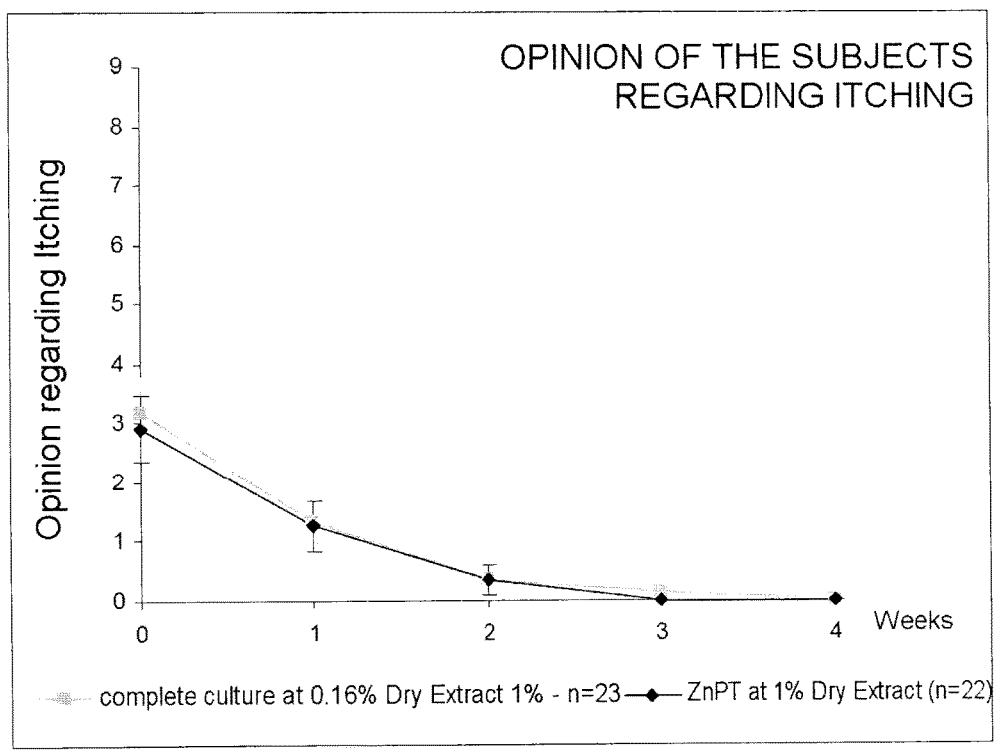
FIG. 11 shows the comparative results of effects on itching of the scalp (opinion of the subjects), obtained using a shampoo formulation in accordance with the invention comprising 0.16% by weight of the active agent (bacterial lysate in the complete fermentation medium), relative to the total weight of the dry extract of the formulation.

The results are given in FIGS. 10 and 11.

FIG. 10 shows the comparative results of effects on itching of the scalp (opinion of the subjects), obtained using a shampoo formulation in accordance with the invention comprising 0.32% by weight of the active agent (bacterial lysate in the complete fermentation medium), relative to the total weight of the dry extract of the formulation. The reference comparative formulation comprises 1% by weight of active agent, relative to the total weight of the dry extract.

FIG. 11 shows the comparative results of effects on itching of the scalp (opinion of the subjects), obtained using a shampoo formulation in accordance with the invention comprising 0.16% by weight of the active agent (bacterial lysate in the complete fermentation medium), relative to the total weight of the dry extract of the formulation. The reference comparative formulation comprises 1% by weight of active agent, relative to the total weight of the dry extract.

The invention claimed is:

1. A process for preventing, treating, or both preventing and treating dandruff condition of an individual, the process comprising:
administering to an individual in need thereof, one lysate of a bacterium, said lysate consisting of a lysate of a bacterium belonging to the genus of *Vitreoscilla*, and being administered with all or parts, in terms of amount, of a complete fermentation medium, said complete fermentation medium resulting from the culturing process having been used for the growth and the cell lysis of said bacterium, said medium having undergone no additional manipulation aimed at separating and/or removing all or part of its non-aqueous constituents,
wherein said lysate with complete fermentation medium comprises:
cytoplasmic fractions,
cell wall fragments,
metabolites formed, released, or both formed and released during cell lysis of said bacterium, and
water-soluble metabolites generated and released spontaneously by said bacterium in the fermentation medium.

2. The process of claim 1, wherein the bacterium is *Vitreoscilla filiformis* strain.

3. The process of claim 1, wherein the bacterium is *Vitreoscilla filiformis* (ATCC 15551) strain.

4. The process of claim 1, wherein the process is carried out topically.

5. The process of claim 1, wherein the dandruff condition is associated with at least one condition of a proliferation of pathogenic microorganisms on a scalp and an imbalance of scalp ecoflora in the individual.

6. The process of claim 1, wherein the genus of *Vitreoscilla* is *Vitreoscilla filiformis*.

7. The process of claim 1, wherein said complete fermentation medium is taken directly from the culturing process and has not undergone any additional manipulation aimed at separating and/or removing other than sterilization of its non-aqueous constituents.

8. The process of claim 7, wherein the bacterium is *Vitreoscilla filiformis* strain.

* * * * *

UNITED STATES PATENT AND TRADEMARK OFFICE
CERTIFICATE OF CORRECTION

PATENT NO.       : 10,046,014 B2
APPLICATION NO.  : 14/110049
DATED            : August 14, 2018
INVENTOR(S)      : Pascal Hilaire It is certified that error appears in the above-identified patent and that said Letters Patent is hereby corrected as shown below:

On the Title Page

Item (56), U.S. Patent Documents, Line 9, "2011/0014246" should read --2011/0014248--

Item (56), Other Publications, Lines 1-2, "PCT/IB12/051696" should read --PCT/IB12/051698--

Signed and Sealed this
Thirtieth Day of July, 2019

Andrei Iancu
*Director of the United States Patent and Trademark Office*